US010251989B2

(12) United States Patent
Cook et al.

(10) Patent No.: US 10,251,989 B2
(45) Date of Patent: Apr. 9, 2019

(54) COMPACT PULMONARY ASSIST DEVICE FOR DESTINATION THERAPY

(71) Applicant: CARNEGIE MELLON UNIVERSITY, Pittsburgh, PA (US)

(72) Inventors: Keith E. Cook, Pittsburgh, PA (US); David Skoog, Pittsburgh, PA (US)

(73) Assignee: CARNEGIE MELLON UNIVERSITY, Pittsburgh, PA (US)

( * ) Notice: Subject to any disclaimer, the term of this patent is extended or adjusted under 35 U.S.C. 154(b) by 284 days.

(21) Appl. No.: 15/289,003

(22) Filed: Oct. 7, 2016

(65) Prior Publication Data

US 2017/0021082 A1 Jan. 26, 2017

Related U.S. Application Data

(63) Continuation of application No. PCT/US2015/024799, filed on Apr. 7, 2015.

(60) Provisional application No. 61/995,301, filed on Apr. 7, 2014.

(51) Int. Cl.
*A61M 1/16* (2006.01)
*B01D 63/02* (2006.01)

(52) U.S. Cl.
CPC .......... *A61M 1/1698* (2013.01); *B01D 63/02* (2013.01); *B01D 2313/105* (2013.01); *B01D 2313/20* (2013.01); *B01D 2313/21* (2013.01)

(58) Field of Classification Search
CPC .. A61M 1/1698; B01D 2313/21; B01D 63/02
See application file for complete search history.

(56) References Cited

U.S. PATENT DOCUMENTS

| 4,374,802 | A | 2/1983 | Fukasawa |
| 4,722,829 | A | 2/1988 | Giter |
| 4,791,054 | A | 12/1988 | Hamada et al. |
| 5,162,101 | A | 11/1992 | Cosentino et al. |
| 5,922,202 | A * | 7/1999 | Elgas .................. A61M 1/1698 210/321.8 |
| 2002/0190000 | A1 | 12/2002 | Baurmeister |
| 2003/0028073 | A1 | 2/2003 | Mochizuki et al. |
| 2010/0125235 | A1 | 5/2010 | Cauley, III et al. |

FOREIGN PATENT DOCUMENTS

WO 2015100288 A1 7/2015

OTHER PUBLICATIONS

International Search Report and Written Opinion of the International Searching Authority for PCT Application PCT/US2015/024799 dated Jul. 8, 2015.
European Search Report for European Application 15776535.5 dated Oct. 30, 2017.

* cited by examiner

*Primary Examiner* — Leslie R Deak
(74) *Attorney, Agent, or Firm* — Michael G. Monyok; David G. Oberdick

(57) ABSTRACT

The present invention relates generally to a pulmonary assist device comprising a housing having tapered inlets and outlets to distribute blood evenly over a fiber bundle. The fiber bundle has a relatively low packing density to prevent the formation of clots. The invention is adapted to be used with a pump or without a pump, in which the heart supplies the necessary blood flow. Moreover, the device can be used as a single module or as multiple modules arranged in parallel.

16 Claims, 9 Drawing Sheets

| Type of Pulm Disease | CO calc (LPM) | Final Device Flow | Sweep gas Flow (LPM) | Device flow/CO calc (%) | Est. DO2 (ml/min) | Est. CO2 (ml/min) |
|---|---|---|---|---|---|---|
| Hypercapnic (COPD) | 3.9 | 0.8 – 1.1 | 1 | 25% | 69 | 72 |
| Hypoxemic | 4.2 | 2.8 | 2.2 | 67% | 117 | 126 |
| Pulm. Htn. | 4.3 | 2.3 | 1.5 | 53% | 105 | 119 |

| APACHE II | $PaO_2:FiO_2$ | pH | $CO_2$ |
|---|---|---|---|
| 24.3 +/- 7.8 | 58.3 +/- 13.1 | 7.21 +/- 0.13 | 96.3 +/- 27.2 |

COMPACT PULMONARY ASSIST DEVICE FOR DESTINATION THERAPY

CROSS-REFERENCE TO RELATED APPLICATIONS

This application claims the benefit under 35 U.S.C. § 120 of Application No. PCT/US2015/024799, filed Apr. 7, 205, which claims the benefit under 35 U.S.C. § 119 of U.S. Provisional Application Ser. No. 61/995,301, filed Apr. 7, 2014, each of which are incorporated by reference herein in their entirety.

STATEMENT REGARDING FEDERALLY SPONSORED RESEARCH

Not applicable.

BACKGROUND OF THE INVENTION

The invention relates generally to a pulmonary assist device. More specifically, the invention relates to a compact pulmonary assist device used for oxygenating blood and/or removing carbon dioxide and which can be used for extended periods of time without suffering from performance degradation due to clots forming in the device.

Chronic lung diseases, such as chronic obstructive pulmonary disease (COPD), cystic fibrosis (CF), and idiopathic pulmonary fibrosis (IPF), are one of the leading causes of death and morbidity in the world. In the United States alone, there are over 12 million chronic lung disease patients, with approximately 140,000 deaths resulting annually from the disease. The only definitive treatment for these patients is lung transplantation, yet there are only 1,700 lung transplantations per year with an estimated 50% survival at 5 years after implantation.

Those living with the disease suffer from frequent acute exacerbations of the disease state, severely reducing their quality of life. Patients ultimately experience a progressive decline in respiratory function with right heart failure from pulmonary hypertension. These patients can be maintained with oxygen therapy and pulmonary vasodilators, but not without frequent exacerbations requiring hospitalization, inflicting exorbitant cost to the patients as well as the health care system in general. However, there are no devices capable of providing long-term support for these patients and lung transplantation is the only viable treatment.

Even if a patient is designated to receive a lung transplant, many require support while waiting for donor lungs to become available. Gas exchangers, or oxygenators, used for short-term cardiopulmonary bypass are typically only used for a few hours. Other types of gas exchangers used for long-term use can include thoracic artificial lungs (TALs), devices for arterio-venous carbon dioxide removal ($AVCO_2R$), extracorporeal membrane oxygenation (ECMO) devices, and respiratory dialysis. These devices are largely differentiated by how these devices achieve a blood supply, where the blood is returned to the patient, and whether or not a pump is used.

Mechanical ventilation is insufficient as a long-term support mechanism for patients awaiting a transplantation because it leads to muscle atrophy, lung infection, respiratory and systemic inflammation, multi-organ failure, and poor outcomes after transplantation. In the past, ECMO had been deemed insufficient as a bridge to lung transplantation due to poor outcomes during extended waiting periods. However, improvements in ECMO technology and a change in Lung Allocation Scores, which assigns priority for who will receive a transplant, drove a re-examination of this therapy. The new lung allocation system shortened wait list times, reducing the period of support required by a bridge. Median wait list times while on ECMO are thus typically 3-12 days, but many patients wait far longer.

Despite the recent advances, ECMO support is still prone to progressive complications which limit its application. For example, patients undergoing ECMO must receive regular blood product transfusions. Platelet consumption and acquired von Willebrand's disease lead to bleeding complications. Additionally, ECMO oxygenators typically fail due to clot formation within a few weeks, leading to risk of thromboembolic complications and requiring device replacement. As a result, survival to transplantation decreases with length of time on ECMO and common complications, including infections and multi-organ failure, can prohibit transplantation even if a patient survives.

Further complicating treatment, premature initiation of ECMO may lead to progressive complications and reduced survival, but if not initiated soon enough, patients may progress to irreversible organ damage. Although a few patients have been supported beyond 30 days, it is critically important to quickly find organs for patients on ECMO waiting for lung transplantation. Thus, ECMO used as a bridge to transplantation is often only considered in well-selected young patients with rapid deterioration of their lung disease in the absence of other organ dysfunction.

For example, patients with primary pulmonary hypertension were treated with a low resistance gas exchanger, the Novalung® ILA, and were successfully bridged. Although successful, the Novalung® ILA is not designed for destination therapy as it lacks sufficient $O_2$ transfer to support patients with respiratory failure and provides only marginal unloading of the RV. Thus, when the ILA is used in the ECMO setting, patients remained on mechanical ventilation. Perhaps most importantly, the ILAs failed due to clot formation after 10-12 days on average. Thus, it is not ideally suited as either a bridge to lung transplantation or destination therapy device.

Arterio-venous carbon dioxide removal ($AVCO_2R$) is another therapy used as a bridge to lung transplantation. In $AVCO_2R$ therapy, blood flows into a compact gas exchanger and is pumpless, which is thought to cause significantly less blood activation than ECMO and may be better suited for long-term support. Although the $AVCO_2R$ approach allows for effective CO2 transfer, it supplies less than 10% of a patient's oxygen requirements. Furthermore, the AV shunt forces the heart to increase cardiac output to maintain peripheral circulation, making $AVCO_2R$ unsuitable for patients with pulmonary hypertension and right ventricle dysfunction.

Other types of devices, such as cardiopulmonary bypass oxygenators, can assist lung function but are designed to be used for just a few hours or days. Oxygenators are used mostly to support patients undergoing open-heart surgery, for example, so the device is not intended to be used as a bridge to transplantation. Rather, the devices are designed with short-term performance in mind. While the devices perform well in these limited duration settings, the devices tend to clot after a few days. To use currently available oxygenators as a bridge to transplantation, the patient would have to swap the device every several days, which carries significant health risks.

While lung transplantation is the only viable treatment for chronic lung disease due to the drawbacks of current devices used for long-term support, many patients require only partial support to attain acceptable oxygen and carbon dioxide transfer and the unloading of their failing right ventricle. It would therefore be advantageous to develop a pulmonary assist device that provides necessary oxygen and carbon dioxide transfer levels and is capable of being used for extended periods of time.

BRIEF SUMMARY OF THE INVENTION

According to embodiments of the present disclosure is a pulmonary assist device for destination therapy. In one embodiment, the pulmonary assist device comprises a fiber bundle and a housing for the bundle that additionally provides a fluid path for blood passing through the bundle. Blood enters through an inlet on one side of the housing, passes through the fiber bundle, and exits thorough an outlet on the opposite side of the housing. Oxygen gas or an oxygen gas mixture is pumped through the interior of the hollow fibers in order to oxygenate the blood passing over the fibers and to remove carbon dioxide. Each end of the fibers in the bundle is enclosed by a gas distribution manifold to direct gas through the fibers. The spaces occupied by the blood and oxygen are kept separate to prevent the risk of introducing air bubbles into the blood and the exchange of gases occurs through the walls of the fibers. Direct contact between the blood and gas can cause negative effects on the blood.

The pulmonary assist device (PAD) of the present invention can be used by chronic lung disease patients for a period of several months to years (with device replacement), allowing them to return home and live a relatively normal life. The device could thus serve as a bridge to lung transplantation or as a means of permanent, destination therapy.

According to some embodiments, the PAD possesses the major advantage of greater longevity than other commercial gas exchangers, which typically fail due to clot formation over a period of 1-4 weeks, even with surface coatings intended to slow coagulation. In addition, in some embodiments blood flow through the PAD can be driven by the right ventricle, which eliminates the need for an external pump. The lack of a pump decreases the size and weight of the device, increases wearability, and decreases blood damage and associated complications over long-term use. Additionally, it eliminates an additional, expensive component that can fail during long-term use. Allowing the right ventricle to drive blood flow also allows the patient's own heart to control gas exchange, leading to a more normal physiology and less complicated, compact product. In alternative embodiments, the PAD can also be coupled with a pump to support the patient with combined cardiopulmonary failure, for example.

DETAILED DESCRIPTION OF THE INVENTION

Figure 1A:
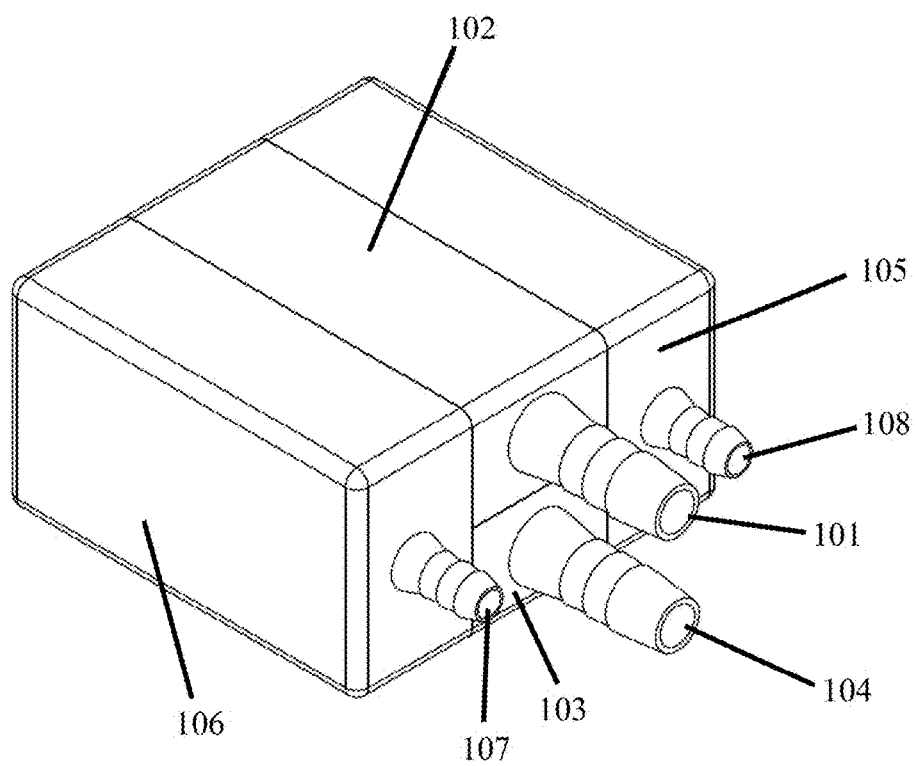
FIG. 1A shows a pulmonary assist device according to one embodiment of the present invention.

Embodiments of the present invention and its advantages are best understood by referring to FIGS. 1A-7. FIG. 1A shows an integrated PAD with a view of the external components. In typical use, blood from a patient enters the device through inlet 101 of top housing 102. The exterior of inlet 101 is slightly tapered to allow a friction fit between the inlet 101 and a tube carrying the blood to the PAD. The tubing can be plastic tubing, but a person of ordinary skill will appreciate that any medical tubing can be used to transport blood to the device. For a more secure connection, clamps can be secured on the tubing where it engages blood inlet 101 and outlet 104. After entering the top surface 230 of a fiber bundle 201 contained within the device, through the fiber bundle 201, and exiting a bottom surface 220 of the bundle 201, the blood exits through outlet 104 contained on bottom housing 103. In the embodiment shown in FIG. 1A, housing 102 and housing 103 are identical copies. However, in alternative embodiments, the size or shape of each housing 102/103 may differ. For example, in one embodiment, the housings 102/103 are a single unit.

Further shown on FIG. 1A are gas distribution caps 105 and 106, which distribute oxygen or other gases into the fiber bundle 201. Distribution cap 105 (also referred to as a gas manifold) contains an inlet 108 to allow passage of oxygen or another gas into the fiber bundle 201. Distribution cap 106 similarly contains an outlet 107 to allow the removal of gases from within the fiber bundle 201, which will be a mix of oxygen, carbon dioxide, and other gases. In one particular method of operation, the gas outlet 107 is under a slight vacuum to prevent the risk of bubbles being forced into the blood within the device. Alternatively, in the one embodiment, each fiber 210 of the fiber bundle 201 has a layer of polydimethylsiloxane (PDMS) to eliminate the need for a vacuum on the outlet.

Figure 1B:
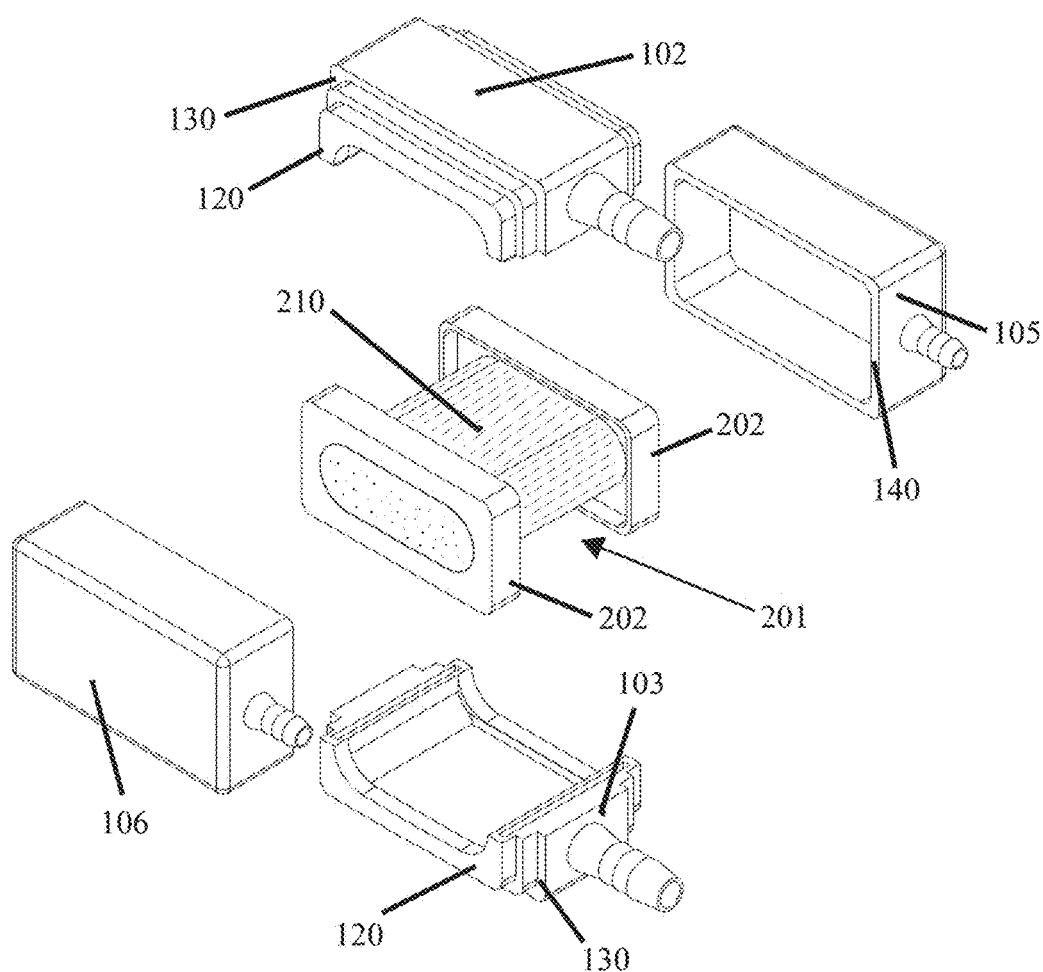
FIG. 1B is an expanded view of the pulmonary assist device showing various components of the device.

FIG. 1B is an exploded view of the PAD. In FIG. 1B, the fiber bundle 201 is shown surrounded by top housing 102, bottom housing 103, and the gas distribution manifolds 105 and 106. In the embodiment shown in FIG. 1B, the fiber bundle 201 is terminated with end caps 202, which are formed around the bundle 201 with a potting material such as polyurethane, polydimethylsiloxane (PDMS), or epoxy-like materials. To create the endcaps 202, the top housing 102 and bottom housing 103 are placed around bundle 201. At this point, the fibers 210 comprising the bundle 201 are loose and there is not yet separation between the blood section and the gas section of the PAD. With the housings 102 and 103 in place around the bundle 201, a potting material is poured onto the ends of fibers 210 and within ridge 120 of the housings 102 and 103. The potting material fills the space between each fiber 210 and additionally bonds the fiber bundle 201 to the housings 102 and 103. To expose the lumens, or interiors of the fibers 210, a portion of the potting material is removed from each end of the bundle 201. The exposed fibers 210 are shown as region 204 in FIG. 3. While some potting material is removed from the ends of fibers 210, a portion of the potting material remains between the fibers 210 to serve as a barrier between the blood and gas.

Alternatively, the end caps 202 can be pre-formed and shaped to fit within ridge 120. A tight fit between ridge 120 and end cap 202 or the addition of a sealer between the two ensures there is no leakage between the section of the PAD containing blood and the section containing the exchange gas. In some embodiments, housings 102 and 103 include a secondary ridge 130 located adjacent to ridge 120 which is shaped to engage a rim 140 of the gas manifolds 106 and 105. During assembly, the gas manifolds 106 and 105 are attached to the housings 102 and 103 with epoxy, solvent bonding, or welding techniques. In one embodiment, the housings 102 and 104 and gas distribution manifolds 105 and 106 are injection molded from a biocompatible polymer, such as polycarbonate. Inlets 101 and 108 and outlets 104 and 107 can be reinforced with materials such as titanium or stainless steel.

Figure 2:
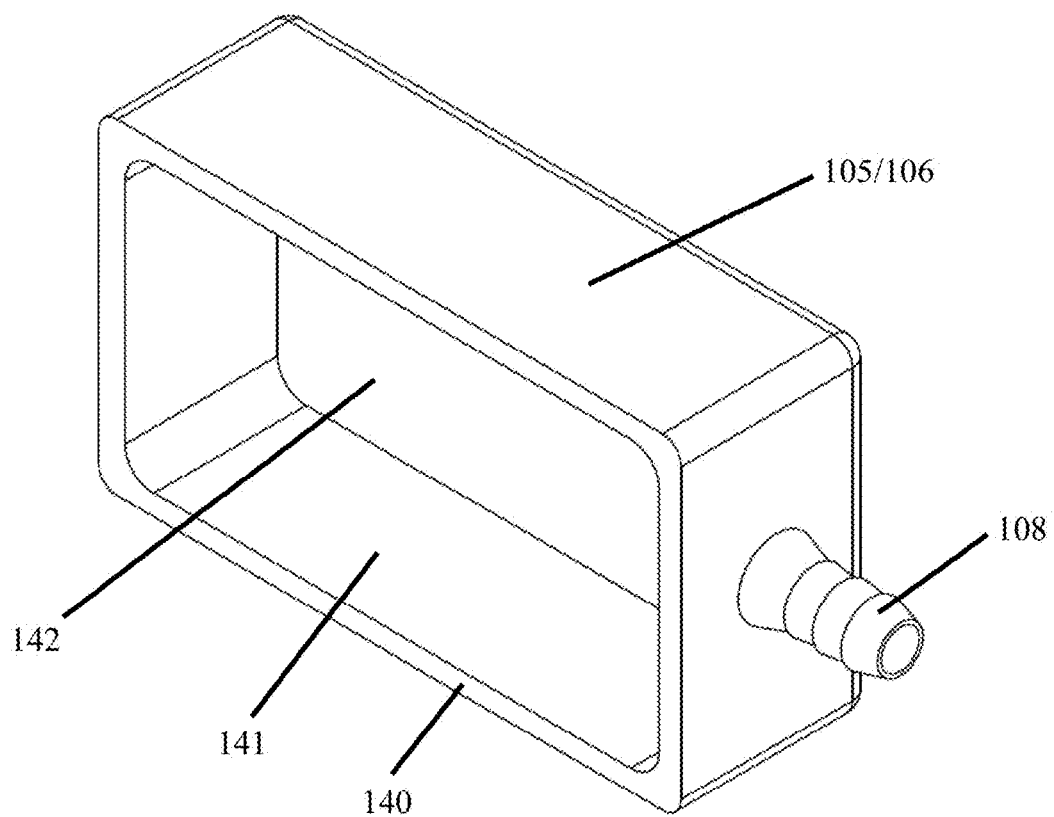
FIG. 2 depicts a gas distribution manifold according to one embodiment.

FIG. 2 shows the details of one of the gas distribution manifolds 105 or 106. Manifold 105 can be similarly shaped to manifold 106, as shown in FIGS. 1A-1B. In this example embodiment, to reduce manufacturing costs, the same housing can be used for both sides of the PAD. However, in alternative embodiments, the two manifolds 105 and 106 can be shaped differently. Referring again to FIG. 2, the interior of gas distribution manifold 105/106 is shown to include a generally open interior portion defined by interior side surface 141 and interior top surface 142. When assembled in the PAD, a portion of rim 140 and interior surface 141 of the manifold 105/106 fittingly engages ridge/surface 130 of the housings 102 and 103. The end cap 202 does not press against interior top surface 142 or interior surface 141, but rather a volume between the end cap 202 and the interior top surface 142 is maintained to allow free movement of gas entering through inlet 108 and across the width of manifold 105/106. Inlet 108 and outlet 107 can be oriented in any manner on manifolds 105/106, depending on the orientation of the device. In one embodiment, outlet 107 is in a vertical, downward facing orientation so that any condensate from the gas is able to freely flow out of outlet 107 with gravity. A similar gap is maintained in the gas exit manifold 106.

Figure 3:
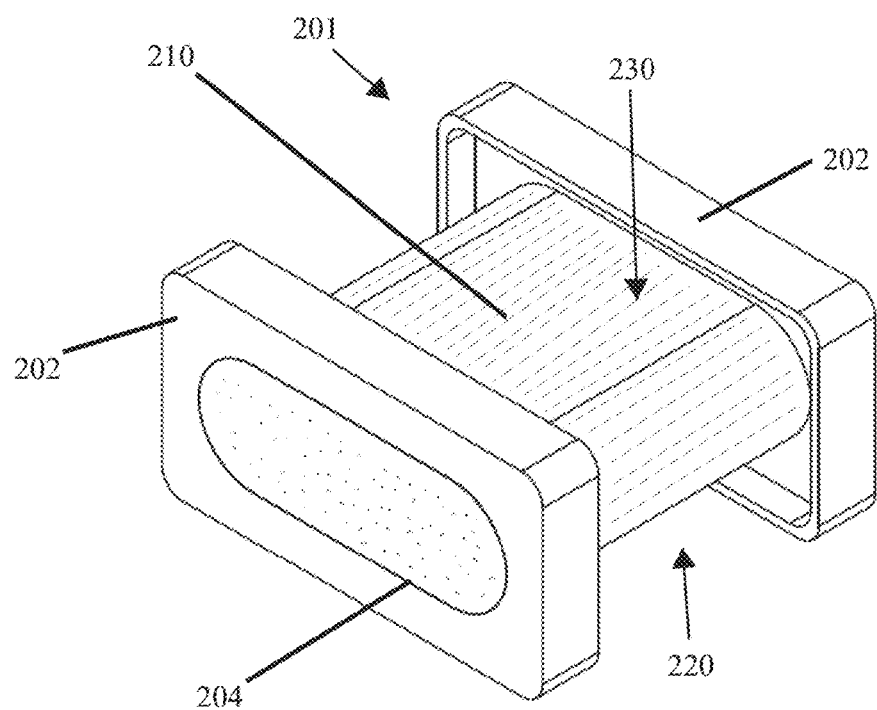
FIG. 3 shows a fiber bundle with end caps at each end of the bundle.
Figure 11:
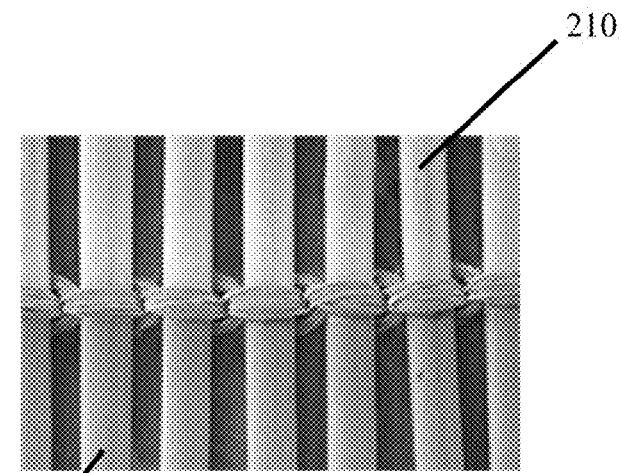
FIG. 11 is a magnified view of the fibers comprising the fiber bundle.

FIG. 3 is a detailed view of fiber bundle 201 with end caps 202. The path of oxygen pumped through the fibers runs generally length-wise from a first end cap 202 to the end cap 202 on the opposite side of the bundle 201. The fiber bundle 201 is comprised of a plurality of individual fibers 210. In one embodiment, each fiber 210 is constructed of polypropylene with an outside diameter of about 200 microns. The fibers can also be constructed of polymethylpentene or other suitable materials. In addition, the fibers 210 can be of any diameter up to about 380 microns. A magnified view of individual fibers 210 which are grouped together to form fiber bundle 201 is shown in FIG. 11. Larger fibers lead to a larger fiber bundle 201 size, thus larger prime volume for similar performance.

Additionally, the fibers 210 can be coated with PDMS to prevent plasma from passing through the hollow fiber 210 and to prevent bulk flow of gas from the fiber 210 into the blood of the patient, which would cause an air embolism. Plasma leakage can occur after a few days of use as the surface of the porous wall of the fiber 210 transitions from hydrophobic to hydrophilic after deposition of proteins and other molecules. A bulk flow of gas can occur when the pressure of the gas in the fiber bundle 201 exceeds the blood pressure in the PAD. Such a situation can arise when the gas outlet 107 or its associated tubing is accidentally blocked, for example. Antithrombogenic coatings can also be applied to the fibers.

Figure 12:
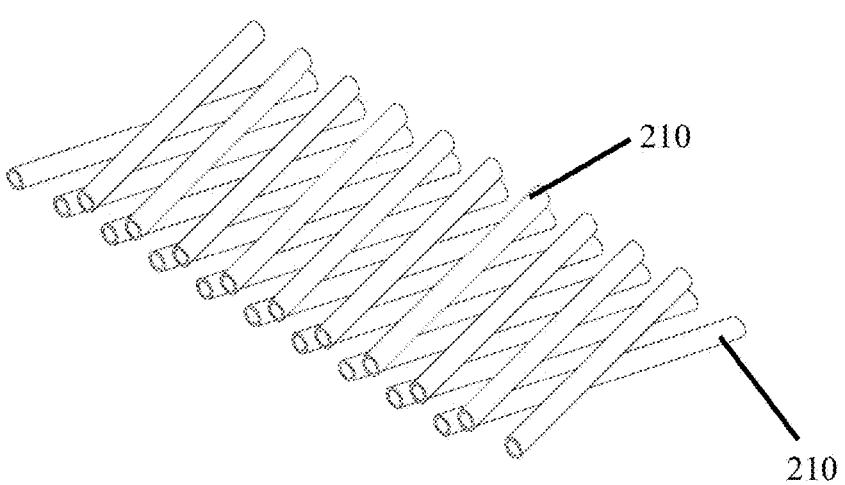
FIG. 12 is a schematic depicting two layer of fibers comprising the fiber bundle.

The fibers 210 can be knit together into a thin, gauzy fabric. One layer of the fabric is shown in FIG. 11. Two layers of fibers 210 are shown in FIG. 12, with one layer rotated relative to the other to maintain fiber 210 spacing. The fabric can be wound around some core to form the fiber bundle 201, which forms the gas transfer membrane of the device. The fiber bundle 201 has a packing density of less than about 30%, in one embodiment, to reduce clot formation. In another embodiment, the fiber bundle has a density of about 27%, within a range of +/−1%. However, any fiber bundle 201 with a density less than 50% will show improved clot resistance. The percent packing density of the fiber bundle is defined as 100 times the volume of space occupied by fibers 210 divided by the total volume of the fiber bundle 201. It is calculated solely by the outside diameter of fiber 210 and its spacing within the fabric in fibers/cm.

The fibers 210 are arranged, grouped, or woven into fiber bundle 201 having a fiber surface area of around 0.375-0.400 $m^2$ in one example embodiment. A larger area can provide greater gas exchange between the oxygen passing through the interior of the fibers 201 and the blood passing around the outside of the fibers 201, but a greater surface area can cause larger hematological changes as more blood components bind and activate on the fiber bundle 201. As such, the bundle 201 construction can vary depending on the patient and their disease state. For a given fiber size and spacing, the resistance is dependent on the total surface area of the bundle 201, the frontal area of a top surface 230, and the bundle 201 thickness. If two of these variables are known, the third variable can be calculated to set the resistance. In one embodiment, the PAD can have a resistance equal to or less than the resistance of a diseased human lung and close to the resistance of a healthy lung. In the embodiment shown in FIG. 3, the fiber bundle 201 has a frontal area of 35 $cm^2$ and a path length (or depth) of about 2.53 cm. These measurements are provided by way of example and are not intended to limit the scope of the invention. The dimensions of the fiber bundle 201 can vary depending on the intended application. Ultimately, the fiber bundle 201 must maintain adequate gas exchange performance while presenting a low packing density to prevent clotting.

Figure 4:
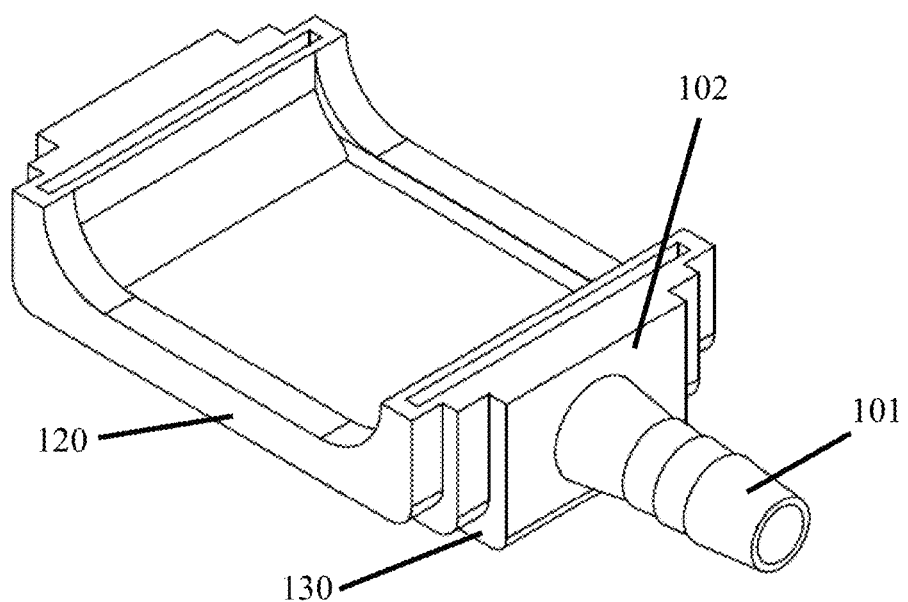
FIG. 4 shows one section of the housing.
Figure 5:
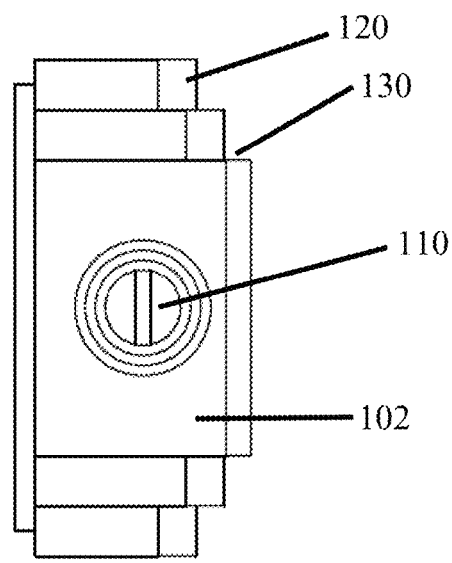
FIG. 5 is an alternate view of the section of housing viewed along the axis of the inlet.

FIG. 4 shows a detailed view of housing 102, according to one embodiment. Similar to the gas distribution manifolds 105 and 106, housings 102 and 103 can be shaped the same. Thus, the description of housing 102 applies to housing 103 as well. However, in alternate embodiments, the inlet housing 102 and outlet housing 103 can be shaped differently. For example, a tapered nozzle 110 on inlet housing 102 creates a uniform distribution, but the same tapered nozzle 110 on the outlet housing 103 could lead to a region of high sheer stress on the blood. In this example, the outlet (or bottom) housing 103 would not have the same tapered nozzle 110. Inlet 101 provides an outer surface that provides an area of engagement with a conduit carrying the blood to the PAD. While a particular inlet 101 is shown as an example in FIG. 4, a person of ordinary skill in the art will appreciate that any device or structure providing an adequate connection could be used. The interior of inlet 101 is hollow to allow the passage of blood from the exterior of the PAD to the interior. Also shown in FIG. 4 are ridges, or surface areas, 120 and 130, which provide mating surfaces for the end caps 202 and gas distribution manifolds 105/106, respectively. FIG. 5 is an alternate perspective of the housing 102, viewed along a line coaxial with the centerline of the inlet 101. As can be seen in greater detail in FIGS. 6-7, nozzle 110 is visible on the interior of housing 102.

Figure 6:
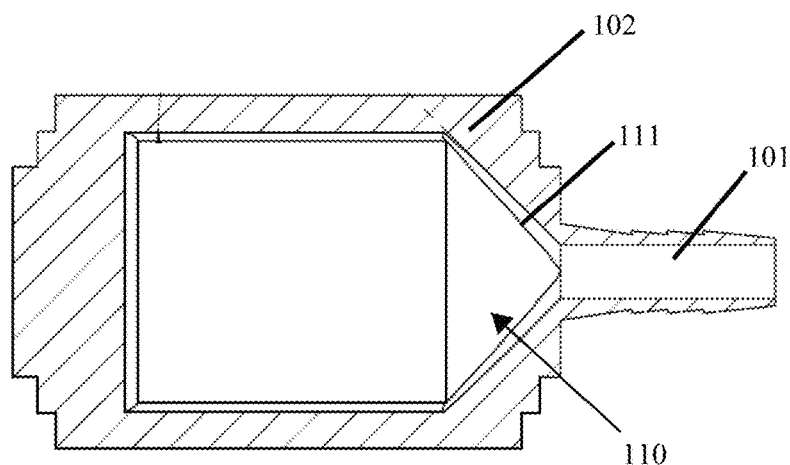
FIG. 6 is yet another view of the section of housing, showing a cross-sectional view with a taper of a diffuser visible.
Figure 7:
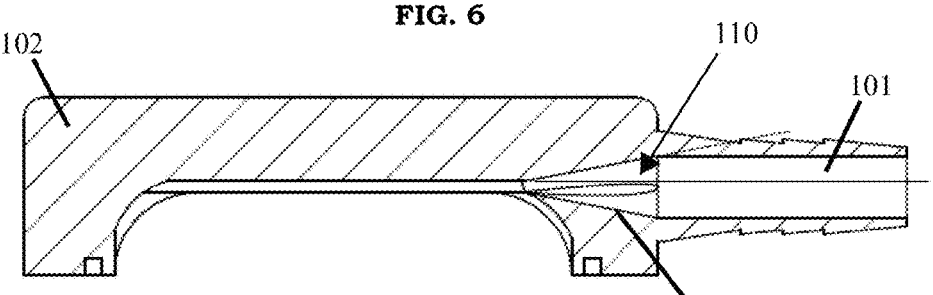
FIG. 7 is an alternate cross-sectional view of the section of housing.

As shown in FIG. 6, which is a cross-sectional view of the inlet housing 102 across its width, nozzle or diffuser 110 is located on the interior of housing 102 just downstream of inlet 101. The diffuser 110 expands from about the diameter of the inlet 101 to substantially the width of housing 102. In one embodiment, the horizontal sidewalls 111 of nozzle 110 are tapered between 30 and 45 degrees, as measured from the centerline of the inlet 101, to make a smooth transition from the narrow diameter of inlet 101 to the greater width of the housing 102. If the inlet 101 terminated at an interior wall of the housing 102 without a transition (i.e. using 90 degree interface rather than a 30-45 degree taper), then the blood entering the housing 102 would flow as a straight jet into the housing 102 and the flow could become disrupted, with recirculations and jetting forming in certain locations, particularly the lateral edges of the housing 102. These recirculations and stagnant regions lead to clot formation. The combination of the vertical contraction (as seen in FIG. 7) with the lateral expansion (as seen FIG. 6) in diffuser 110 eliminates the jet and provides an even distribution of blood across the fiber bundle 201. This eliminates regions where clots can form.

FIG. 7 shows a cross-sectional view of housing 102, where the housing 102 is bisected through its height. As can be seen in FIG. 7, nozzle 110 further comprises vertical sidewalls 112 which are tapered towards each other along a direction from the distal end of inlet 101 to the interior of housing 102. Stated differently, vertical sidewalls 112 tend to constrict the blood flow as it enters the housing 102. With the horizontal sidewalls 111 expanding and vertical sidewalls 112 constricting, the velocities of the blood flow are equalized. Like the horizontal sidewalls 111 of nozzle 110, the vertical sidewalls 112 form a gradual taper, according to one embodiment. The angle of taper is about 5-15 degrees from the centerline of the inlet. The housing 102, especially the shape of the nozzle 110, is designed so as to ensure even blood flow across the fiber bundle 201. This even blood flow ensures efficient gas exchange, reduces blood flow resistance due to blood recirculation and, as previously stated, reduces locations where blood can clot.

Figure 13A:
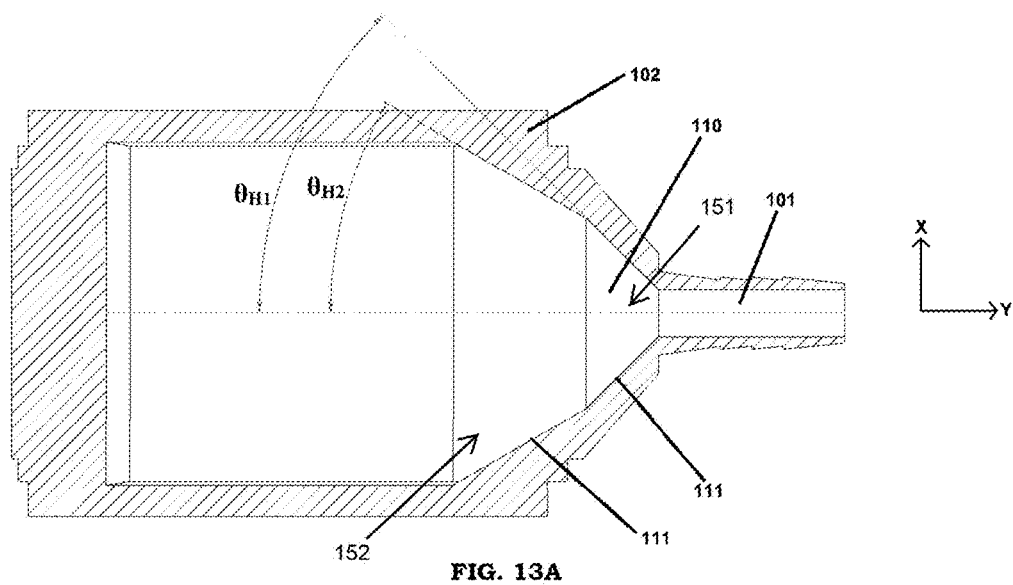
FIGS. 13A-13C depict the pulmonary assist device according to an alternative embodiment.
Figure 13B:
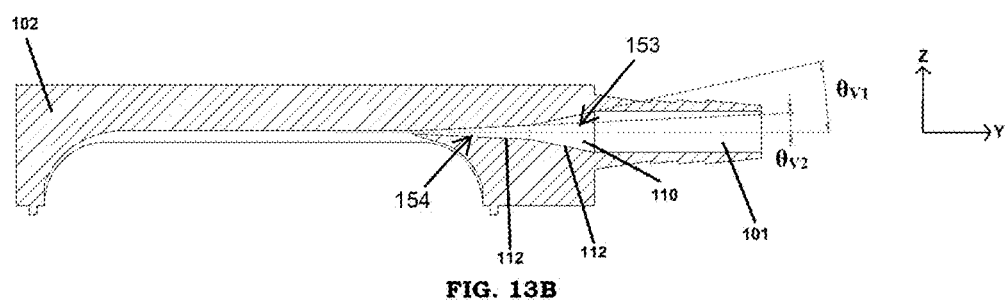
Figure 13C:
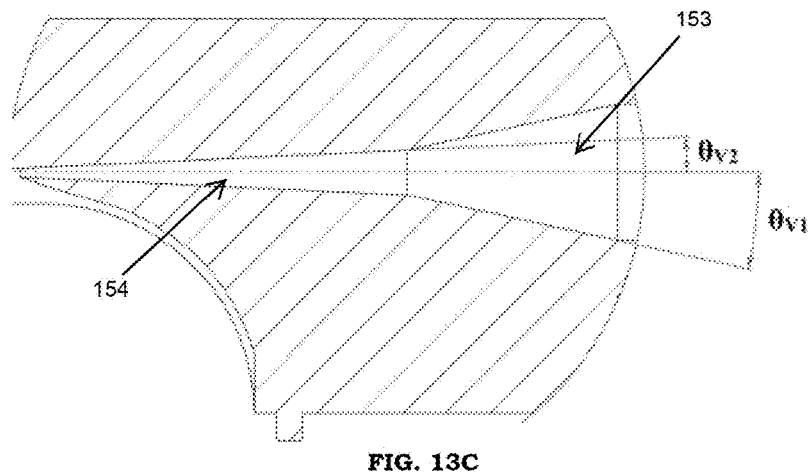

In an alternative embodiment, nozzle 110 or diffuser expansion and contraction occurs in two stages prior to blood flowing into the fiber bundle 201, as shown in FIGS. 13A-13C. FIG. 13A shows a cross-sectional view of housing 102, where the housing is bisected along the X-Y plane. As can be seen in FIG. 13A, nozzle or diffuser 110 expands in a first stage 151 from about the diameter of the inlet 101, then in a second stage 152 to substantially the width of housing 102. In the first stage 151 of the nozzle 110, the horizontal sidewalls 111 of nozzle 110 are tapered at an angle, $\theta_{H1}$, between 15 and 60 degrees (as measured from the centerline of inlet 101) to make a smooth transition from the narrow diameter of inlet 101 to the greater width of the second stage 152. In the second stage 152, the horizontal sidewalls 111 of nozzle 110 are tapered at an angle, $\theta_{H2}$, between 15 and 60 degrees (as measured from the centerline of inlet 101) to make a smooth transition from the narrow width of the beginning of the second stage 152 to the greater width of the second stage 152. While a range of angles have been provided, the angle ($\theta_{H1}$) of the first stage 151 is generally larger or smaller than the angle ($\theta_{H2}$) of the second stage 152. Depending on the particular combination of the first stage 151 and the second stage 152, the two-stage nozzle 110 can further reduce prime volume and improve the uniformity of the velocity profile of the blood before it passes through the fiber bundle 201.

FIG. 13B shows a cross-sectional view of housing 102 of the alternative embodiment, where the housing is bisected along the Y-Z plane. As can be seen in FIG. 13B, nozzle 110 further comprises vertical sidewalls 112 which are tapered towards each other in two stages along a direction from the distal end of inlet 101 to the interior of housing 102. In the first stage 153, the vertical sidewalls 112 of nozzle 110 are tapered at an angle, $\theta_{V1}$, between 0 and 45 degrees (as measured from the centerline of inlet 101) to make a smooth transition from the greater diameter of inlet 101 to the narrower width of the beginning of second stage 154 of the inlet nozzle 110. In the second stage 154, the vertical sidewalls 112 of nozzle 110 are tapered at an angle, $\theta_{V2}$, between 0 and 45 degrees (as measured from the centerline of inlet 101) to make a smooth transition from the greater width of the beginning of the second stage 154 to the narrower width of the end of the second stage 154. FIG. 13C is a more detailed view of the vertical sidewalls 112 in the first stage 153 and the second stage 154 in nozzle 110.

The nozzle 110 can use a two-stage design in only the horizontal direction, only the vertical direction, or both the horizontal and the vertical direction. With the two stages 151,152 of the horizontal sidewalls 111 expanding and the vertical sidewalls 112 constricting, the velocities of the blood flow are equalized prior to the blood entering into the region of the interior of the housing 102 where the fiber bundle 201 is located. In one example embodiment, nozzle 110 expands with angles $\theta_{H1}$ and $\theta_{H2}$ equal to 30 degrees, and constricts with angle $\theta_{V1}$ equal to 7.125 degrees and angle $\theta_{V2}$ equal to 1.349 degrees. In this example, with $\theta_{H1}$ and $\theta_{H2}$ being equal, the horizontal sidewalls 111 are constant, similar to a single stage nozzle 110.

Figures 8, 9, 10:
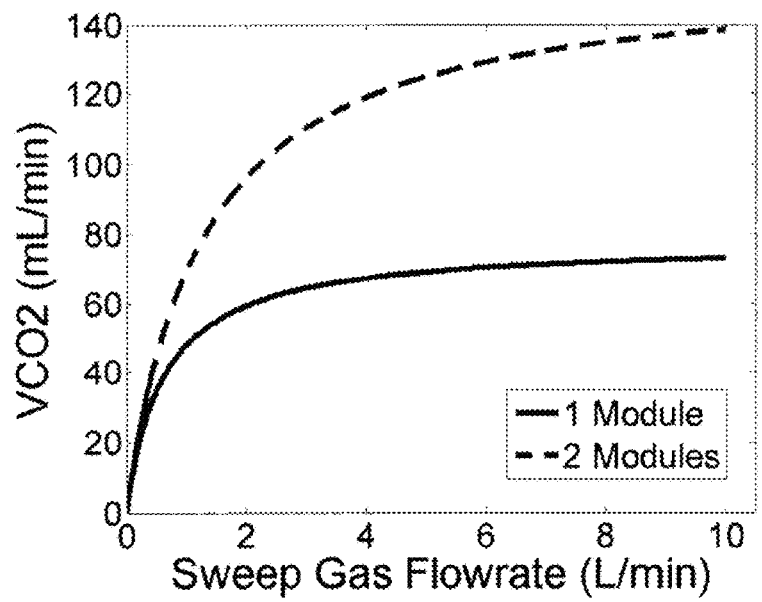
FIG. 8 is a graph showing the relative performance of a single module compared to two modules used in parallel.
FIG. 9 is a chart showing the performance of an oxygenator according to a prior art device for patients with different types of respiratory diseases.
FIG. 10 is another chart depicting performance.

The shape of the nozzle 110 diffuses the blood in the horizontal direction on the inlet housing 102 and a gathers the blood in the horizontal direction on the outlet housing 103. That is, nozzle 110 affects fluid flow based on the direction of travel of the blood. The housing 102 shape results in a device with low resistance and efficient gas exchange, meeting the needs of a variety of chronic lung diseases with one PAD or two modules in parallel. In one example embodiment, the resistance of the fiber bundle 201 for each module is approximately 0.665 mmHg/(L/min), yielding a total module resistance of about 1.94 mmHg/(L/min) at a flowrate of 1.25 L/min. Each module is capable of increasing blood oxygen saturation from 65% to >95% at the 1.25 L/min rate of blood flow, allowing for a total allowable blood flow through the system to exceed 2.5 L/min with two modules in parallel. Placing two modules in parallel yields a system resistance of 0.97 mmHg/(L/min), not including tubing and tubing connections. A two-module PAD will also transport >125 ml/min of CO2 using reasonable sweep gas flow rates. The relative $CO_2$ exchange performance of a single module or two modules used in parallel is shown in FIG. 8.

When attached in parallel and in a PA-LA configuration, the PAD can be used without a pump, which eliminates the large circuit present with ECMO. In the pumpless implementation, the heart adjusts its output as needed to modulate gas exchange, and the PAD can be run with a 5% $CO_2$/95% $O_2$ gas mixture, for example, that allows for a fixed gas flow rate. Most important for long-term use, the PAD's low blood-flow resistance, low shear stresses, and the lack of a pump, heat exchanger, and reservoir cause a marked reduction in coagulation, inflammation, and damage to formed elements in blood as compared to ECMO devices. Thus, unlike ECMO, no blood products need to be given during PAD use. Lastly, use in this configuration reduces the need for close monitoring, including the adjustment of pump and gas flow rate, and this reduces the cost of care.

In one embodiment, the PAD of the present invention can attach to the pulmonary circulation with blood flowing from the proximal pulmonary artery (PA) to the inlet 101 of the PAD and returned from the outlet 104 to either the left atrium (LA) in PA-LA attachment or to the distal PA in PA-PA attachment. The right ventricle drives blood through the PAD, obviating the need for a mechanical pump, in some embodiments. In alternative embodiments, the PAD can draw and return blood flow to any of the larger veins or arteries with or without a pump.

In an example embodiment, the PAD can provide the following functionality: 1) receive up to 2.5 L/min of cardiac output 2) achieve >95% $O_2$ saturation of this blood, 3) remove up to 125 ml/min of $CO_2$, 4) develop less than a 100% increase in resistance over a period of 3 months, and 5) incorporate gas exchange fibers that eliminate plasma and gas leakage to ensure maintenance of gas transfer and exclusion of air emboli. To achieve these parameters, which require low resistance, two devices can be used in parallel since each module will have a fiber bundle resistance of 0.665 mmHg/(L/min) and an overall device resistance of 1.94 mmHg/(L/min). A two module system lowers the overall resistance to about 0.97 mmHg/(L/min). The resistance figures are given as an example and will vary depending on the size and density of the fiber bundle 201 and the shape of nozzle or diffuser 110.

As stated previously, the PAD has a packing density of about 25%. Depending on the particular application, a packing density of less than 50% can be used, which is the standard fiber packing density for cardiopulmonary bypass oxygenators. This standard of 50% has been adopted by long-term artificial lungs intended for any application. These include the MC3 BioLung™ TAL, Novalung® ILA, and Maquet Quadrox-D, amongst others. The design philosophy of cardiopulmonary bypass (CPB) oxygenators is focused on minimizing priming volume, which is the open volume within the oxygenator that must be filled with a fluid before being attached to a patient. Due to their short duration of use (typically a few hours), coagulation is not a significant problem. However, prime volume is a concern for these uses. Cardiopulmonary bypass circuits are large, and must be primed with 1,400-2,000 ml of fluid. This can be either crystalloid solutions (saline, Lactated Ringers, etc) or blood. The greater the crystalloid volume in the prime is, the lower the hematocrit is during and after cardiopulmonary bypass. Lower hematocrit is thought to lead to a higher complication rate following cardiopulmonary bypass and is thus avoided. Alternatively, one may use blood transfusions to correct this, but this also leads to complications. Thus, low prime volume is highly valued, and all bypass oxygenator manufacturers attempt to lower it as a marketing tool. As a result, CPB oxygenators all feature fiber bundles with a packing density around 50%. This allows CPB oxygenators to meet their gas transfer requirements with low priming volume.

These types of oxygenators have been on the market for 30 or so years, and this design philosophy has been around since their inception. It is standard practice for the industry, and thus fiber bundles are customarily made with this specification. In designing long-term, hollow-fiber "artificial lung" devices, it appears that device manufacturers follow CPB design norms based on this history. However, a packing density of 50% leads to clot formation within a relatively short time of use. Thus, the present invention utilizes a fiber bundle 201 that is wide (large cross sectional area for blood flow), thin (short distance that blood must flow through the device), and with a low packing density (~25%, for example).

A low packing density results in a low surface area to blood volume ratio (SA:V), which leads to lower concentrations of procoagulants in the blood stream. The industry norm for SA:V is approximately 100-140 $cm^2$/ml of blood volume. The fiber bundle 201 of the present invention has a value of 63 $cm^2$/ml. It also means that the spacing between adjacent fibers is larger (170-220 microns at 50% packing vs. 457 at 25% packing density). Thus, a small layer of adhered protein or clot causes less of a change in resistance in the low packing density bundle 201. As a result, clot formation in the PAD develops more slowly, what does form has minimal effect on performance, and the functional lifetime of the device is longer than conventional oxygenators or artificial lungs with greater packing densities.

With the PAD of the present invention, it is possible to tailor the studied and developed approaches to the specific pathophysiologic derangements of pulmonary failure. Essential to this analysis is understanding the amount of unloading required by the RV and the $O_2$ and $CO_2$ transfer needed to achieve an acceptable correction of the patient's pathophysiological state. A review of this data led to a critical insight: only partial support is needed to improve patients clinical status and allow them to become ambulatory. The performance of an ECMO device with patients having end stage lung disease is shown in FIG. 9. The percentage of device flow compared to calculated cardiac output verifies that full support is not necessary.

The analyzed patient mobilization data further demonstrates the ability to liberate bed-bound patients with severe pulmonary disease and permit them to participate in physical therapy and maintain their nutritional status independently. Whether the goals of care were bridge to transplantation or bridge to recovery, their performance improvement was remarkable with only partial replacement therapy. FIG. 10 summarizes the patient's pre-ECMO physiologic state, emphasizing the severely decompensated state of these patients.

While the disclosure has been described in detail and with reference to specific embodiments thereof, it will be apparent to one skilled in the art that various changes and modifications can be made therein without departing from the spirit and scope of the embodiments. Thus, it is intended that the present disclosure cover the modifications and variations of this disclosure provided they come within the scope of the appended claims and their equivalents.

What is claimed is:

1. A device to assist pulmonary function, comprising:
   a fiber bundle having a first end and a second end, wherein the fiber bundle is comprised of a plurality of hollow fibers;
   a housing surrounding the fiber bundle between the first end and the second end, the housing comprising:

an inlet nozzle in fluid communication with an inlet,
wherein the inlet nozzle simultaneously expands in a horizontal plane and constricts in a vertical plane along a blood flow path, and an outlet nozzle in fluid communication with an outlet, wherein the blood flow path is established from the inlet, through the inlet nozzle, through the fiber bundle, through the outlet nozzle, and to the outlet;

a first gas distribution manifold surrounding the first end of the fiber bundle, a second gas distribution manifold surrounding the second end of the fiber bundle, wherein the second gas distribution manifold is in fluid communication with the first gas distribution manifold through an interior of at least a portion of the plurality of hollow fibers.

2. The device of claim 1, further comprising:
a gas inlet attached to the first gas distribution manifold; and
a gas outlet attached to the second gas distribution manifold,
wherein a gas flow path is established from the gas inlet, through the interior of at least a portion of the plurality of hollow fibers, to the gas outlet.

3. The device of claim 2, further comprising:
end caps formed on each of the first end of the fiber bundle and the second end of the fiber bundle,
wherein the end caps are sealing engage the housing to separate the blood flow path from the gas flow path.

4. The device of claim 1, the inlet nozzle further comprising:
a horizontal sidewall that tapers at an angle from a line coextensive with the blood flow path,
a vertical sidewall that tapers at an angle from a line coextensive with the blood flow path.

5. The device of claim 4, wherein the inlet nozzle vertical sidewall tapers at a first angle in a first stage of the inlet nozzle and a second angle in a second stage of the inlet nozzle.

6. The device of claim 4, wherein the inlet nozzle horizontal sidewall tapers at a first angle in a first stage of the inlet nozzle and a second angle in a second stage in the inlet nozzle.

7. The device of claim 5, wherein the first angle is larger than the second angle.

8. The device of claim 6, wherein the first angle is larger than the second angle.

9. The device of claim 1, wherein the outlet nozzle constricts in a horizontal plane and expands in a vertical plane along the blood flow path.

10. The device of claim 9, the outlet nozzle further comprising:
a horizontal sidewall that tapers at an angle from a line coextensive with the blood flow path,
a vertical sidewall that tapers at an angle from a line coextensive with the blood flow path.

11. The device of claim 1, wherein a volume of the plurality of hollow fibers is less than 30% of a volume of the fiber bundle.

12. The device of claim 11, wherein the volume of the plurality of hollow fibers is 27% of the volume of the fiber bundle.

13. The device of claim 1, wherein each fiber of the plurality of hollow fibers has an outside diameter of about 200 microns.

14. The device of claim 1, wherein each fiber of the plurality of hollow fibers has a layer of polydimethylsiloxane disposed on a surface of each fiber.

15. The device of claim 1, wherein each fiber of the plurality of hollow fibers is coated with an antithrombogenic agent.

16. The device of claim 1, wherein the blood flow path is orthogonal to the gas flow path.

* * * * *